United States Patent [19]
Kirchner

[11] Patent Number: 5,535,485
[45] Date of Patent: Jul. 16, 1996

[54] TYING DEVICE FOR BODY PARTS

[75] Inventor: Claudia Kirchner, Markgröningen, Germany

[73] Assignee: Kimetec GmbH, Ditzingen, Germany

[21] Appl. No.: 313,216

[22] PCT Filed: Mar. 25, 1993

[86] PCT No.: PCT/EP93/00721

§ 371 Date: Sep. 28, 1994

§ 102(e) Date: Sep. 28, 1994

[87] PCT Pub. No.: WO93/19677

PCT Pub. Date: Oct. 14, 1993

[30] Foreign Application Priority Data

Mar. 28, 1992 [DE] Germany ............... 42 10 255.3
Jul. 2, 1992 [DE] Germany ............... 9208869 U

[51] Int. Cl.⁶ ................................... A61B 17/132
[52] U.S. Cl. ..................... 24/170; 24/614; 606/203
[58] Field of Search ........................ 606/203; 24/323, 24/324, 170, 191, 614–616

[56] References Cited

U.S. PATENT DOCUMENTS 2,882,903  4/1959  Ramien ........................ 606/203
4,561,437  12/1985  Kirchner ...................... 606/203

FOREIGN PATENT DOCUMENTS 2321264  3/1977  France .
126465  10/1900  Germany ........................ 24/191
3602778  8/1987  Germany .
WO88/00456  1/1988  WIPO .

Primary Examiner—James R. Brittain
Attorney, Agent, or Firm—Jansson & Shupe, Ltd.

[57] ABSTRACT

A constriction device for limiting circulation of blood, fluids and other materials to limbs and other appendages. Compressive force can be applied to the limb or other appendage through the device's band which is held in place by the action of a clamping member. Compressive force may be variably or immediately released. The device is convenient to use and may be controlled with one hand leaving the other hand free to perform other tasks.

21 Claims, 1 Drawing Sheet

U.S. Patent   Jul. 16, 1996   5,535,485
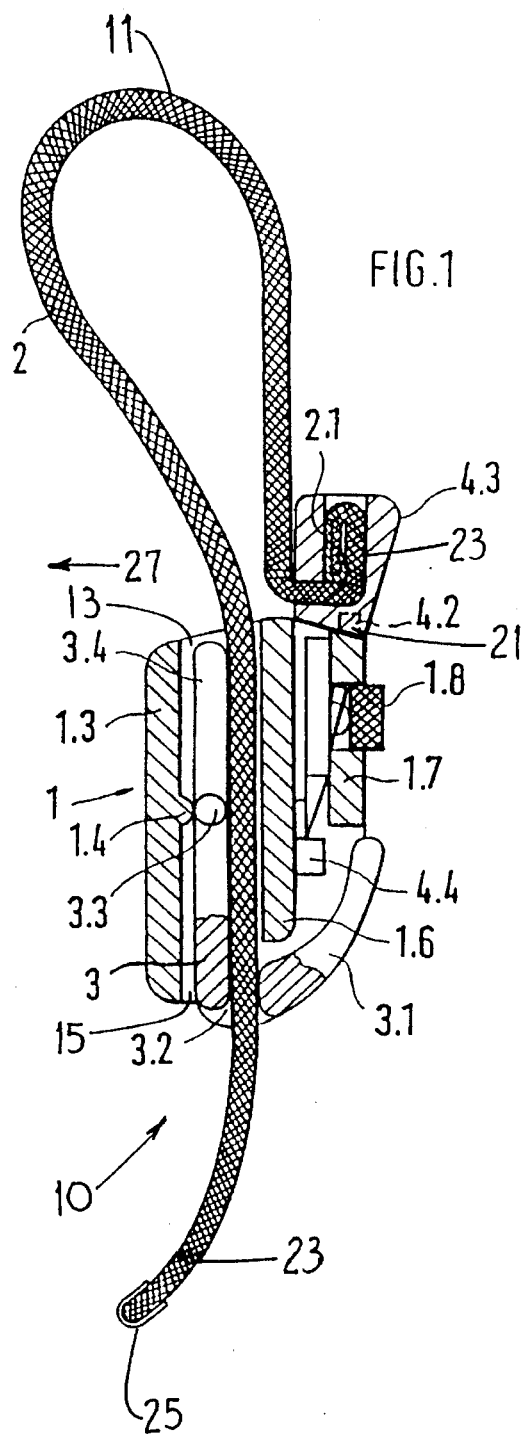
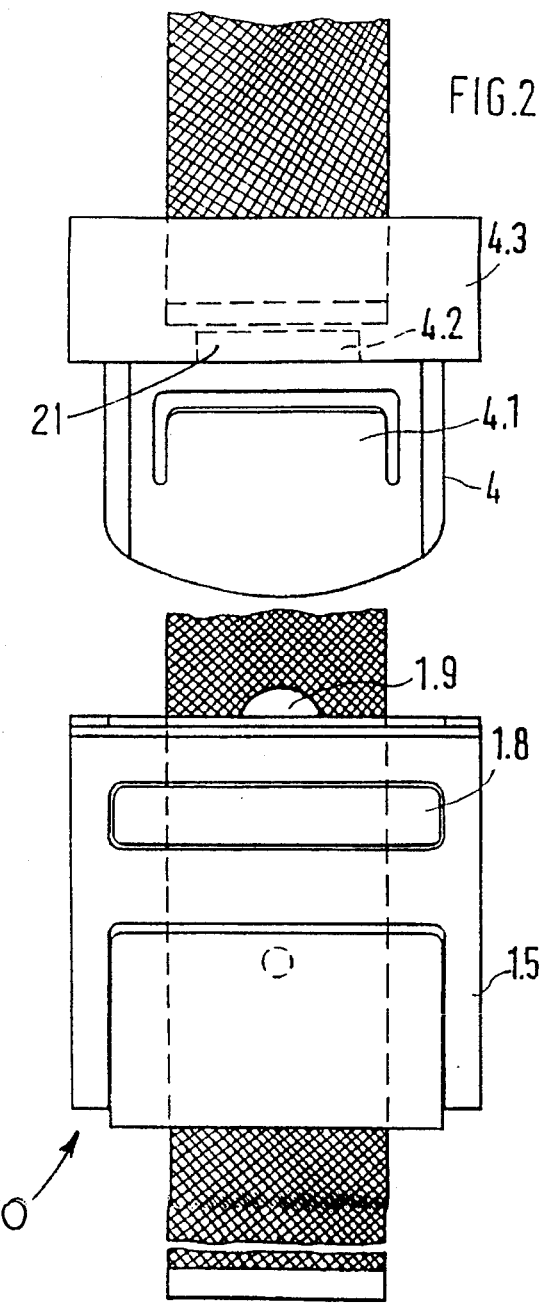

TYING DEVICE FOR BODY PARTS

FIELD OF THE INVENTION

This invention is related generally to constriction devices and, more particularly, to tourniquet-type devices for arresting flow of blood, fluids and other materials in a limb or other appendage by compression.

BACKGROUND OF THE INVENTION

The invention relates to a constriction device particularly useful to medical and other health-related professions for limiting circulation of blood, fluids and other materials to limbs and other appendages. The invention includes a lock housing, a bottom wall, center wall, two lateral walls, a covering wall on the upper side, and an elastic constriction band that is attached at one end to the lock housing by means of an engaging shoe. The free end of the band is guided through the lock housing between the bottom wall and the center wall forming a loop in the band. A clamping member swivelably supported in the lock housing is provided to clamp the band between a plate-like section of the clamping member and the center wall.

The invention further includes an actuation part mounted on the end of the clamping member plate-like section furthest from the loop. The actuation part extends approximately across the width of the plate-like section of the clamping member at its point of attachment and has an insertion opening for the free end of the band. The clamping member may be supported in corresponding holes of the lateral walls and/or on a strip which is provided on the bottom wall, by means of lateral axle sections.

A constriction device of this type is purportedly known from DE 36 02 778 A1. With this known device only the upper side of the lock housing is provided above the clamping member to act as a support when fastening the band. The actuation part used to loosen the loop protrudes forward at the lock housing. This embodiment is disadvantageous with regard to ease of handling.

Another constriction device is purportedly known from DE 38 40 007 A1. The band is provided with an engaging shoe on one side which engages in a lock housing in a coupling manner. The other end of the band is guided over the bottom part of the lock housing by forming a loop, and is fastened against the bottom with a clamp lever. No further information is given on the design and use of the clamp lever.

Another constriction device is specified in DE 38 39 794. This device primarily describes the recessed positions in the lateral housing walls which mate with the axle pins of the swivelably supported clamp lever. Further information in this case regarding the clamping mechanism is also not provided.

Other prior art constriction devices are illustrated in EP 0 196 646 A2, DE 34 31 728 A1, DE 25 36 620 C2, DE 25 41 433 C2, DE 33 14 099 C2 and DE 36 24 112 A1. These constriction devices are less than satisfactory because they are relatively costly, (particularly as a result of the clamping devices), or because they are awkward and difficult to handle.

OBJECTS OF THE INVENTION

It is an object of this invention to provide a constriction device overcoming some of the problems and shortcomings of devices of the prior art.

One object of this invention is to provide a constriction device capable of applying continuous compressive force to a limb or other appendage, thus restriction the flow of blood, fluids and other matter.

Another object of this invention is to provide a constriction device capable of operation with one hand, and particularly with the thumb and forefinger of the hand.

Yet another object of this invention is to provide a constriction device capable of gradual release of compressive force on a limb or other appendage.

It is also an object of this invention is to provide a constriction device capable of immediate and complete release of compressive force on a limb or other appendage.

An additional object of this invention is to provide a constriction device which is lightweight and easily made of inexpensive materials.

These and other important objects will be apparent from the following descriptions and from the drawings, wherein:

SUMMARY OF THE INVENTION

This invention is a tourniquet-type device useful for, among other things, temporarily stopping bleeding or for arresting the circulation of blood by compression. For example, the device could be used to limit blood flow in a limb such as an arm or leg. The device is compact and can be easily handled with one hand.

The device includes a lock housing having a center wall and a clamping member having a plate-like section. The center wall is arranged as a support over the clamping member plate-like section, parallel to a bottom wall and fixed to the lock housing. A slight gap is formed between the center wall and clamping member when the clamping member is in a parallel position. The gap is larger than the thickness of the band.

The lock housing further includes a cover wall which is shorter than the plate-like section of the clamping member at the end of the lock housing furthest from the loop. The invention further includes an actuation part attached to the end of the clamping member furthest from the loop. The actuation part is bent toward the back and extends close to the side of the cover wall and, relative to the top of the cover wall, is flush or protrudes slightly when in the clamp position.

As a result, the constriction device assumes not only a very compact, handy form, but it can also be operated more easily and more accurately, since pressure from the thumb on the actuation device is mainly exerted centrally on the lock housing as it is held in the hand. A slow release in an easy manner is thereby made possible, so that the operator does not need to concentrate excessively on the operation of the tying device and is not distracted from the services being provided to the patient, such as monitoring of measurement values. In addition, the design of the invention is attractive and creates a favorable visual impression.

A particularly useful design of the lock housing can be achieved if the plate-like section of the clamping member, the actuation part and the lateral axle sections are formed as one part. Good lever action for clamping the band and for releasing it by means of the actuation part arises if the plate-like section extends across the length of the bottom wall or protrudes over the front side of the bottom wall facing the loop.

According to the invention, the end of the band may also be easily disengaged from the lock housing by use of the operator's thumb. This desirable result is made possible because the band is detachably fastened at one end to the lock housing by an engaging tongue of an engaging shoe. The tongue is inserted in the lock housing and is snapped into a recess of the cover wall. The tongue, and attached band, can be released by means of a press part arranged in the recess. This desirable arrangement permits the operator to disengage the band while holding the lock housing and without having to change hands.

The engaging shoe attached to one end of the band can be easily released from the lock housing because the tongue includes a spring portion which biases the shoe against the press part. Actuating the press part causes the engaging shoe to easily slide forward against the spring force disengaging the band. Furthermore, the engaging tongue, after snapping in, always rests on the back wall of the recess without play, due to the initial tension exerted by the spring force. When the engaging shoe is pressed down to be released, it slides back as a result of the pre-exerted tension and will not snap back in unintentionally.

Good tracking of the engaging shoe is achieved by having its underside rest on the upper side of the center wall.

The compact shape of the lock housing is enhanced if the engaging shoe has a stop part which abuts that side of the lock housing which faces the band loop. Preferably, the top edge of the engaging shoe is flush with the upper side of the lock housing.

Preferably, the band may be removed from the device and replaced with a different band. To accomplish this desirable result, the stop part includes an undercut groove on its bottom side. The inside width of the undercut groove corresponds to approximately twice the thickness of the band. The band is inserted into the undercut groove with its end folded back and is wedged into the undercut groove. The wedging is enhanced if the end of the band includes a stiff band clamp. The band clamp prevents fraying, produces a wedging effect during traction, and also facilitates the intrusion of the band into the undercut groove.

Preferably, the side of the lock housing that faces the loop is angular to enhance engagement with the engaging shoe. It is also preferred that the engaging shoe include a rounded edge that protrudes toward the loop, which prevents folds of skin from being pulled into the band insertion opening.

Preferably, the side of the lock housing facing the band loop features a projection which, when the engaging shoe is inserted, is pressed into a recess that is present on the facing side of the stop part and is provided with an elastic element. Conversely, the back side of the lock housing may include the recess with the elastic element, and the facing side of the stop part may include the projection. This arrangement further biases the engaging tongue of the engaging shoe against the lock housing, further enhancing disengagement of the engaging shoe and band from the lock housing when the press part is actuated.

Preferably, the elastic element has rubber elasticity or is constructed in the form of a flat spring.

BRIEF DESCRIPTION OF THE DRAWINGS

FIG. 1 is an exemplified embodiment of the constriction device in longitudinal view.

FIG. 2 a top view of the constriction device. The engaging shoe is shown disengaged from the lock housing.

DETAILED DESCRIPTIONS OF THE PREFERRED EMBODIMENTS

FIG. 1 shows an exemplified embodiment of a constriction device 10. FIG. 1 shows lock housing 1, a band 2 formed into a loop 11 and led through lock housing 1, a clamping member 3 positioned in and projecting beyond lock housing 1 and an engaging shoe 4 that is inserted in lock housing 1. Band 2 is connected to the back side of engaging shoe 4 and may be made of a material having elastic properties.

Lock housing 1 has a bottom wall 1.3. Rounded strip 1.4 extends across the width of lock housing 1. Lock housing 1 further includes a cover wall 1.7, two lateral walls 1.5 (see FIG. 2), an opening 13 at the side facing loop 11 and an opening 15 at the side of lock housing 1, through which band 2 can pass. End 23 of band 2 can be provided with a protective edge member 25 (e.g., made of metal). A center wall 1.6 is arranged between the bottom wall 1.3 and the cover wall 1.7. The bottom side of center wall 1.7 faces the upper side of band 2 and contributes to the guidance of band 2 and forms a support against which band 2 is clamped.

In the present exemplified embodiment, the bottom wall 1.3, center wall 1.6 and cover wall 1.7 are aligned parallel to each other. However, this is not a necessary requirement for the operation of constriction device 10. For example, center wall 1.6 can be aligned diagonally to bottom wall 1.3, in order to achieve a more tight or loose fastening effect on the band 2.

The front end of bottom wall 1.3 (the end furthest from loop 11), protrudes further in the exemplified embodiment shown in FIG. 1 than the front end of center wall 1.6. The front end of center wall 1.6, protrudes further than cover wall 1.7 at the upper side of the lock housing 1.

Clamping member 3 has a plate-like section 3.4 positioned between bottom wall 1.3 and center wall 1.6, over which band 2 is guided. The inside width between the plate-like section 3.4. (which is in a center pivoting position), and the underside of center wall 1.6, is sufficiently wide to permit easy passage of band 2, yet sufficiently narrow so that a good fastening effect is accomplished when clamping member 3 is pivoted. Preferably, the gap is slightly larger than the thickness of band 2.

An actuation part 3.1 which is led upward and bent toward the back of lock housing 1 and loop 11 is attached to the front end of clamping member plate-like section 3.4. Actuation part 3.1 is turned toward loop 11. Actuation part 3.1 spans the width of clamping member 3 at the point of attachment, and is preferably integral with clamping member plate-like section 3.4. Because of the variably projecting bottom wall 1.3, the center wall 1.6, the cover wall 1.7 and the actuation part 3.1 can extend in a continuous curve from the front end of clamping member plate-like section 3.4 toward the back of the lock housing 1 and loop 11. The end of the actuation part 3.1 borders near the front side of the cover wall 1.7 and protrudes over its upper side so that it can be pressed down easily to release the clamped band 2. In alternative embodiments, actuation part 3.1 may be designed to project no further than the upper side of cover wall 1.7.

An axle section 3.3 protrudes on each longitudinal side of the plate-like section 3.4 of clamping member 3, inserting into a corresponding recess in each side wall 1.5 of lock housing 1. Preferably, the axle sections 3.3 have a single piece lug shape form on the clamping member plate-like section 3.4.

If strip 1.4 is provided on the bottom wall 1.3 of lock housing 1, it is sufficient to have the recesses of the sidewalls designed longitudinally slotted for the lugs, preventing a movement of clamping member 3 upward in the transverse and longitudinal direction. Strip 1.4 then alone serves to pivot clamping member 3 and to support it from below. If strip 1.4 or an appropriate support is not provided, the recesses in the side walls must be designed as corresponding bore holes, in the form of blind-end or continuous holes.

If lateral walls 1.5 are formed into lock housing 1, the clamping member 3 can be pressed into lock housing 1 and can be snapped or locked by means of axle sections 3.3 into the recesses of lateral walls 1.5. In such embodiment, lateral walls 1.5 and/or clamping member 3 are made of flexible material such as synthetics. For detachment of clamping member 3.3, a tool can be provided that is guided through openings 13 or 15 along the bottom wall 1.3, led past lateral walls 1.5 contacting the axle sections 3.3.

Another variation includes making lateral walls 1.5 detachable, so that they can be emplaced when clamping member 3 is pushed into lock housing 1.

As shown in FIG. 2, engaging shoe 4 features an engaging tongue 4.1 and a stop part 4.3 that encompasses band 2. Engaging shoe 4 is intended to be a recess formed in lock housing 1 by center wall 1.6 and cover wall 1.7. If engaging shoe 4 is pushed in, stop part 4.3 comes to rest against the back side of lock housing 1 which faces loop 11 (refer to FIG. 1). Engaging tongue 4.1 may be made of a flexible resilient material.

The back side of the lock housing 1 expediently features a projection 1.9. Projection 1.9 can be form fitting with recess 21 and elastic element 4.2 which is disposed in recess 21. If engaging shoe 4 is completely pushed in, projection 1.9 pushes against elastic element 4.2. These components bias engaging shoe 4 away from lock housing 1 aiding in disengagement of band 2 from lock housing 1. This arrangement is particularly desirable if the engaging tongue 4.1 does not include a spring portion 17.

At present, elastic element 4.2 fills recess 21 and is designed with rubber elasticity. A flat spring or a similar element, which can be in or on recess 21, can also carry out a similar function. It is understood that elastic element 4.2 can be arranged at the backside of lock housing 1 and the projection 1.9 provided at stop part 4.3. It is important that engaging shoe 4 be pushed back reliably by the effect of the elastic element 4.2 and the counter element 1.9 pushing against it when engaging tongue 4.1 is pushed in, in order to avoid unintentional engagement of the engaging tongue 4.1 and lock housing 1.

Engaging tongue 4.1 snaps into a recess in cover wall 1.7 when engaging shoe 4 is pushed into lock housing 1. Engaging tongue 4.1 rests on a stop wall of press part 1.8 which prevents disengagement of engaging shoe 4 from lock housing 1 when traction load is placed on band 2. Elastic engaging tongue 4.1 can be pushed in and engaging shoe 4 disengaged by means of press part 1.8 which is arranged in the recess and which projects above the upper side of cover wall 1.7. In alternative embodiments, press part 1.8 may be designed to project no further than the upper side of cover wall 1.7.

In order to enable easy release of engagement shoe 4 under traction load, a rounded section, which ensures easy sliding when press part 1.8 is pressed down, is provided on the upper side of engaging tongue 4.1. The front side of engaging shoe 4 can easily move forward toward stop part 1.5 if the engaging shoe 4 is designed to be elastic, while the back side of the engaging tongue 4.1 slides past the stop wall and causes a slight advance of the engaging shoe 4.1. Of course, in this case the stop part cannot abut firmly against the lock housing. As soon as engaging tongue 4.1 is pushed down all the way by depressing press part 1.8, the engaging shoe can slide back, supported by the elastic effect.

If the engaging shoe 4 is pushed in, it comes to rest with its bottom side on the top side of the center wall 1.6. To guide the engaging shoe 4, lateral guides (not shown) alone can be provided as alternatives. The upper side of the stop part 4.3 is aligned with the top side of the cover wall 1.7.

The side of lock housing 1 facing loop 11 is beveled toward the top and the bottom, whereby the edge of those angled bevels is situated between the recess for engaging shoe 4 and opening 13 for the free end of band 2. The bevel points toward loop 11. Any pinching of skin is virtually impossible because the rounded edge can rest on the limb or other appendage.

Stop part 4.3 preferably features, at its bottom side, an undercut groove 23, such that band 2 can be fastened into it. Band 2 is inserted, with its end folded back into the undercut groove 23. To accommodate band 2, the width of groove 23 is equivalent to about twice the thickness of band 2. If band 2 is pulled, it attempts to bulge out and is thereby firmly clamped. This clamping effect is enhanced if there is a stiff band clamp at the end of the band. Band 2, when loosened, can be easily detached from stop part 4.3, so that an exchange of band 2 is possible without the loss of the engaging shoe 4.

In operation, loop 11 of band 2 is placed around an arm or other appendage. End 23 of band 2 is pulled until the appropriate amount of compression is placed on the limb. As band 2 is tightened, a force is exerted in the direction of arrow 27, a vector of which functions to urge that portion of clamping member 3 closest to loop 11 leftward (as viewed in FIG. 1). In response, the portion of clamping member 3 furthest from loop 11 moves rightward (also as viewed in FIG. 1) clamping band 2 between clamping member 3 and center wall 1.6. To intensify the clamping effect, the bottom wall 1.3 can be shorter at the loop 11 side than the plate-like section 3.4. TO avoid any sliding in the clamping position, the upper side of the clamping member plate-like section 3.4 and/or the underside of the center wall 1.6 can be roughened or grooved.

Band 2 may be gradually released by depressing actuation part 3.1 with the operator's thumb. Depressing actuation part 3.1 moves that portion of clamping member 3 furthest from loop 11 leftward releasing the clamping force on band 2 permitting rapid or gradual release of compressive force exerted by band 2.

Band 2 may be immediately disengaged by depressing press part 1.8. Press part 1.8 depresses tongue 4.1 disengaging tongue 4.1 from the stop wall. Elastic element 4.2 biases stop member 4.3 away from lock housing 1. Traction force on band 2 fully disengages engagement shoe 4.3 from lock housing 1.

Overall, the constriction device features a handy, easy to operate design. It can be held easily in one hand because of its compact construction. Compressive force exerted by band 2 can be removed immediately or gradually through use of the operator's thumb. This advantageous and novel design permits the operator to better tend to the needs of the patient or other subject.

While the principles of this invention have been described in connection with specific embodiments, it should be understood clearly that these descriptions are made only by way of example and are not intended to limit the scope of the invention.

What is claimed:

1. A constriction device for limiting circulation of blood, fluids and other materials to limbs and other appendages comprising:

a lock housing having bottom, center and cover walls, the center wall having a first side facing the bottom wall and a second side facing the cover wall, the bottom wall and the center wall first side forming a band-opening therebetween and the center wall second side and cover wall forming a recess therebetween for receiving an engaging shoe;

an elongate band slideably positioned within the band-opening, the elongate band having a first and second end;

an engaging shoe attached to the band first end having a main portion and an engaging tongue protruding therefrom for holding the shoe in engagement with the housing; and a clamping member extending in and along the band-opening and being mounted to pivot about a pivot point, the clamping member having: (a) a first end for engaging the loop, (b) a second end for clamping the band against the center wall, and (c) an actuation part attached to the second end for variably moving the second end away from the center wall; and actuation means secured with respect to the cover wall for detachably engaging the shoe from the housing;

whereby compressive force may be continuously applied to the limb through the band by tightening the loop around the limb thereby causing the clamping member first end to pivot toward the bottom wall and the clamping member second end to pivot toward the center wall to clamp the band between the clamping member second end and center wall and, conversely, compressive force may be variably relieved by depressing the actuation part thereby moving the clamping member second end away from the center wall relieving the clamping force holding the band against the center wall and whereby the band can be removably secured to the housing.

2. The invention of claim 1 wherein the actuation part is curved and has an end facing the loop.

3. The invention of claim 1 wherein the actuation part protrudes slightly beyond the housing when the band is clamped.

4. The invention of claim 1 wherein the actuation part extends across approximately the width of the clamping member.

5. The invention of claim 1 wherein the actuation part includes an opening for passage of the band.

6. The invention of claim 1 wherein the actuation part and clamping member are formed as one piece.

7. The invention of claim 1 wherein the clamping member extends over the length of the bottom wall.

8. The invention of claim 1 wherein the actuation means comprises:

an opening formed in the cover wall; and a press part movably positioned in the opening and projecting into the recess for detachably engaging the shoe from the housing.

9. The invention of claim 8 wherein the press part protrudes slightly beyond the cover wall.

10. The invention of claim 1 wherein the engaging shoe has a bottom side which rests on the center wall second side.

11. The invention of claim 1 further including means for biasing the shoe against the housing.

12. The invention of claim 11 wherein the biasing means comprises:

one of the housing and the shoe having a projection facing the other of the housing and the shoe; and the other of the housing and the shoe having a resilient element for engaging the projection;

whereby the shoe is biased against the housing when the shoe is inserted into the recess.

13. The invention of claim 1 wherein the shoe has a stop part which rests against the housing when the shoe is inserted into the recess.

14. The invention of claim 13 wherein the stop part has a top surface which projects no further than the housing.

15. The invention of claim 1 wherein the shoe has a bottom surface and an undercut groove formed therein for receiving the band first end, the groove having an inside width approximately equivalent to twice the thickness of the band.

16. The invention of claim 15 wherein the band first end is inserted in the groove and is folded back clamping the band in place against the shoe.

17. The invention of claim 16 further including an edge member attached to the band first end.

18. The invention of claim 1 wherein the housing facing the loop is beveled such that the housing between the opening and recess has a rounded edge facing the loop.

19. A constriction device for limiting circulation of blood, fluids and other materials to limbs and other appendages comprising:

a lock housing having opposed bottom and center walls and a band-opening formed therebetween;

an elongate band slideably positioned within the band-opening, the elongate band having: (a) a first end attached to the housing to form a loop for receiving a limb or other appendage, and (b) a free second end; and a clamping member extending in and along the band-opening and being pivotable about a pivot point, the clamping member having: (a) a first end for engaging the loop, (b) a second end for clamping the band against the center wall, (c) an actuation part attached to the second end for variably moving the second end away from the center wall, and (d) a pair of opposed sides;

a pair of opposed lock housing sidewalls, each having a portion facing the band-opening and a recess formed in each such sidewall portion, the recesses being coaxial with one another;

an axle section projecting from each of the opposed clamping member sidewalls, each axle section being received in a separate recess for pivotally supporting the clamping member; and a strip secured to the bottom wall for pivotally supporting the clamping member, whereby compressive force may be continuously applied to the limb through the band by tightening the loop around the limb thereby causing the clamping member first end to pivot toward the bottom wall and the clamping member second end to pivot toward the center wall to clamp the band between the clamping member second end and center wall and, conversely, compressive force may be variably relieved by depressing the actuation part thereby moving the clamping member second end away from the center wall relieving the clamping force holding the band against the center wall.

20. The invention of claim 19 wherein the actuation part includes an opening for passage of the band.

21. The invention of claim 19 wherein the clamping member extends over the length of the bottom wall.

* * * * *

UNITED STATES PATENT AND TRADEMARK OFFICE
CERTIFICATE OF CORRECTION

PATENT NO. : 5,535,485
DATED : July 16, 1996
INVENTOR(S) : Claudia Kirchner It is certified that error appears in the above-identified patent and that said Letters Patent is hereby corrected as shown below:

On the title page, after "[54]", delete the title "TYING DEVICE FOR BODY PARTS" and insert --CONSTRICTION DEVICE-- in place thereof.

In column 1, line 1, delete "TYING DEVICE FOR BODY PARTS" and insert --CONSTRICTION DEVICE--.

Signed and Sealed this

Twelfth Day of November, 1996

Attest:

BRUCE LEHMAN

*Attesting Officer*     *Commissioner of Patents and Trademarks*